(12) United States Patent
Hill et al.

(10) Patent No.: US 8,668,881 B2
(45) Date of Patent: Mar. 11, 2014

(54) VAPORIZED HYDROGEN PEROXIDE DECONTAMINATION STRUCTURE

(71) Applicant: American Sterilizer Company, Mentor, OH (US)

(72) Inventors: Aaron Leif Hill, Madison, OH (US); Thaddeus Joseph Mielnik, Concord, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 13/764,814

(22) Filed: Feb. 12, 2013

(65) Prior Publication Data

US 2013/0216438 A1 Aug. 22, 2013

Related U.S. Application Data

(60) Provisional application No. 61/601,614, filed on Feb. 22, 2012.

(51) Int. Cl.
 *A61L 2/20* (2006.01)
(52) U.S. Cl.
 USPC .......................... 422/292; 422/294; 422/295

(58) Field of Classification Search
 USPC .................................. 422/292, 294, 295, 119
 See application file for complete search history.

(56) References Cited

U.S. PATENT DOCUMENTS

| | | | |
|---|---|---|---|
| 7,189,349 B2 | 3/2007 | Karle | 422/28 |
| 8,216,523 B2 | 7/2012 | Meilander et al. | 422/294 |
| 2007/0098592 A1 | 5/2007 | Buczynski et al. | 422/3 |

OTHER PUBLICATIONS

Int'l Search Report from corresponding Int'l (PCT) Application No. PCT/US13/26014; Dated May 6, 2013, 2 pages.

*Primary Examiner* — Sean E Conley
(74) *Attorney, Agent, or Firm* — Kusner & Jaffe; Michael A. Centanni

(57) ABSTRACT

A decontamination enclosure, comprised of a plurality of preformed panels joined together to form a structure defining a totally enclosed chamber. A door is formed in at least one of the panels, the door being movable between an opened position and a closed position to allow access to the chamber. A circulation system is attached to the structure for circulating vaporized hydrogen peroxide through the chamber. A controller is provided for controlling the amount of vaporized hydrogen peroxide introduced into the chamber.

16 Claims, 6 Drawing Sheets

VAPORIZED HYDROGEN PEROXIDE DECONTAMINATION STRUCTURE

FIELD OF THE INVENTION

The present invention relates generally to disinfection or decontamination of medical devices, and more particularly, to an apparatus for decontaminating non-critical medical devices, such as wheelchairs, IV poles, blood pressure cuffs, case carts and other devices encountered in a hospital environment.

BACKGROUND OF THE INVENTION

Preventing the transmission of infectious diseases is a major concern of all hospitals and medical institutions. Critical items, such as surgical instruments and endoscopes that come into contact with mucus membranes of the body, are sterilized or disinfected between uses to prevent the transmission of communicable diseases.

Non-critical items are those that make contact with intact skin, but not with mucus membranes. Examples of non-critical items include wheelchairs, IV poles, stretchers, patient beds, patient tray tables, computers on wheels, keyboards, blood pressure cuffs, patient furniture, tables and case carts. Just about any device encountered within a hospital, aside from the aforementioned critical items, would be considered "non-critical items." These non-critical items are repeatedly handled by health care workers and other medical staff who substantively come into contact with patients in the course of their duties. It is well known that many types of infectious agents can survive extended periods of time (days to months) on surfaces of non-critical items, and their use and frequent handling by numerous people can contribute to the transmission of infectious agents throughout a hospital.

One method of decontaminating non-critical items is through the use of liquid disinfectants applied through manual cleaning using spray bottles and wiping cloths. As will be appreciated, for certain types of structures, such as wheelchairs, IV poles, patient beds and even computers, it is almost impossible to insure that every surface of the item is decontaminated. Moreover, some hospital devices, such as computers, having air passages therethrough that are used to cool internal electrical components, are particularly difficult to clean.

Another method of disinfecting these non-critical items is to place the items in a dedicated hospital room and expose the entire interior of the room to a decontaminating gas, such as vaporized hydrogen peroxide. To construct such a room in an existing building, requires that door openings and any HVAC outlets or inlets be covered and sealed. When a room in an existing hospital is dedicated for use as a decontamination chamber, great care and significant labor must be employed to insure that all door openings and ventilation ducts are sealed. Some painted surfaces in the room can over time blister and peel due to repeated exposure to vaporized hydrogen peroxide. Moreover, rooms with exterior windows are generally undesirable because during cold months of the year, condensation may occur on cold surfaces. Still further, safety features that insure that hospital workers are not exposed to vaporized hydrogen peroxide during a cycle typically do not exist. In this respect, methods of interlocking the doors or detecting leaks are not available in most hospital settings. In addition, vaporized hydrogen peroxide systems require aeration systems to eliminate the vaporized hydrogen peroxide after a decontamination cycle. As a result, creation of a dedicated room for use as a decontamination room requires considerable structural modifications to the room and surrounding areas. Moreover, once established, such rooms cannot be easily modified or relocated within the hospital infrastructure.

The present invention overcomes these and other problems, and provides a decontamination enclosure for use in hospitals, which decontamination enclosure is modular and may be easily disassembled, relocated and/or expanded.

SUMMARY OF THE INVENTION

In accordance with a preferred embodiment of the present invention, there is provided a decontamination enclosure, comprised of a plurality of preformed panels joined together to form a structure defining a totally enclosed chamber. A door is formed in at least one of the panels, the door being movable between an opened position and a closed position to allow access to the chamber. A circulation system is attached to the structure to circulate gas through the chamber. The circulation system has a duct disposed along the exterior of the structure. The duct is connected to the enclosure and communicates with the chamber at a first location to define an outlet from the chamber and is connected to the enclosure to communicate with the chamber at a second location and at a third location to define inlets to the chamber. A blower is disposed in the duct for conveying a stream of gas through the duct in a first direction. The blower is disposed in the duct downstream from the first location and upstream from the second and third locations. A catalyst is disposed in the duct at the second location. A vaporized hydrogen peroxide generator is connected to the duct for introducing vaporized hydrogen peroxide into the stream of gas at the third location. A controller is provided for controlling the amount of vaporized hydrogen peroxide introduced into the chamber and for controlling the flow of the gas to the second location and the third location.

An advantage of the present invention is a decontamination enclosure for decontaminating medical apparatus.

Another advantage of the present invention is a decontamination enclosure that may be assembled within an existing room or region of a building.

Another advantage of the present invention is a decontamination enclosure that is modular, and can be brought into an existing building in sections and assembled on site.

Another advantage of the present invention is a decontamination enclosure, as described above, that can disassembled in sections and transported to another location and re-assembled.

Another advantage of the present invention is a decontamination enclosure as described above wherein the decontamination enclosure can be expanded, i.e., enlarged.

A still further advantage of the present invention is a decontamination enclosure having one or more doors that allow access to the decontamination enclosure, wherein the doors have sensors and interlocks to prevent access during decontamination cycle.

Another advantage of the present invention is a decontamination enclosure as described above having electrical outlets within the decontamination enclosure to facilitate decontaminating inner passageways of cooling systems for electronic devices.

A still further advantage of the present invention is a decontamination enclosure as described above having sensing means to track and store data with respect to the decontamination of specific items within the hospital.

A still further advantage of the present invention is a decontamination enclosure as described above having feed-back controls that will automatically control the cycle parameters, i.e., sterilant injection rate, and determine when the cycle is complete and the room is safe to enter.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
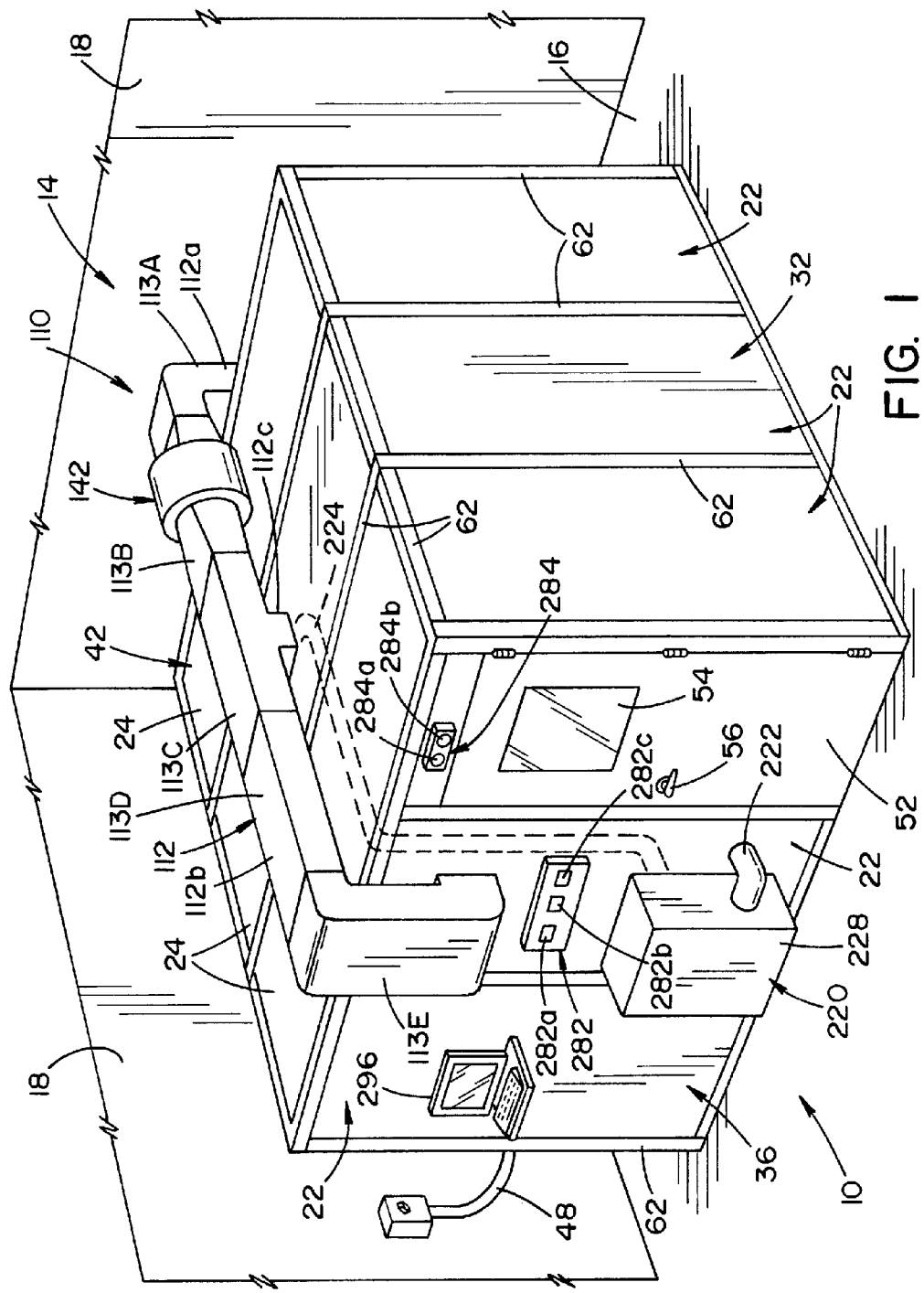
FIG. 1 is a perspective view of a decontamination enclosure illustrating a preferred embodiment of the present invention.

Referring now to the drawings wherein the showings are for the purpose of illustrating a preferred embodiment of the invention only and not for the purpose of limiting same, FIG. 1 shows a decontamination enclosure 10 illustrating a preferred embodiment of the present invention. Enclosure 10 is a modular structure comprised of a plurality of like, pre-formed wall panels 22 and a plurality of like, pre-formed ceiling panels 24 connected together to define an enclosed, sealed decontamination chamber 12, best seen in FIG. 2. In the drawings, decontamination enclosure 10 is shown within a room 14 that is only partially shown. In this respect, decontamination enclosure 10 is disposed on a floor 16 spaced from walls 18 that form the sides of room 14. In FIG. 1, two walls and the ceiling that complete room 14 are not shown. Floor 16 is preferably flat and coated with a material (not shown) inert to vaporized hydrogen peroxide.

Several wall panels 22 are joined together to form a first side 32 of enclosure 10. Similarly, a like number of wall panels 22 are joined together to form a second side 34 of enclosure 10. A front side 36 and a back side 38 are also formed from a plurality of wall panels 22. A plurality of ceiling panels 24 form a ceiling or top side 42 of enclosure 10. At least one wall panel 22 includes a door 52 to allow access to chamber 12 defined by enclosure 10. In the embodiment shown, door 52 is disposed in a wall panel 22 forming front side 36 of enclosure 10. A door seal (not shown) surrounds door 52 so as to hermetically seal door 52 to wall panel 22, as shall be described in greater detail below. In the embodiment shown, door 52 includes a window 54.

Figure 2:
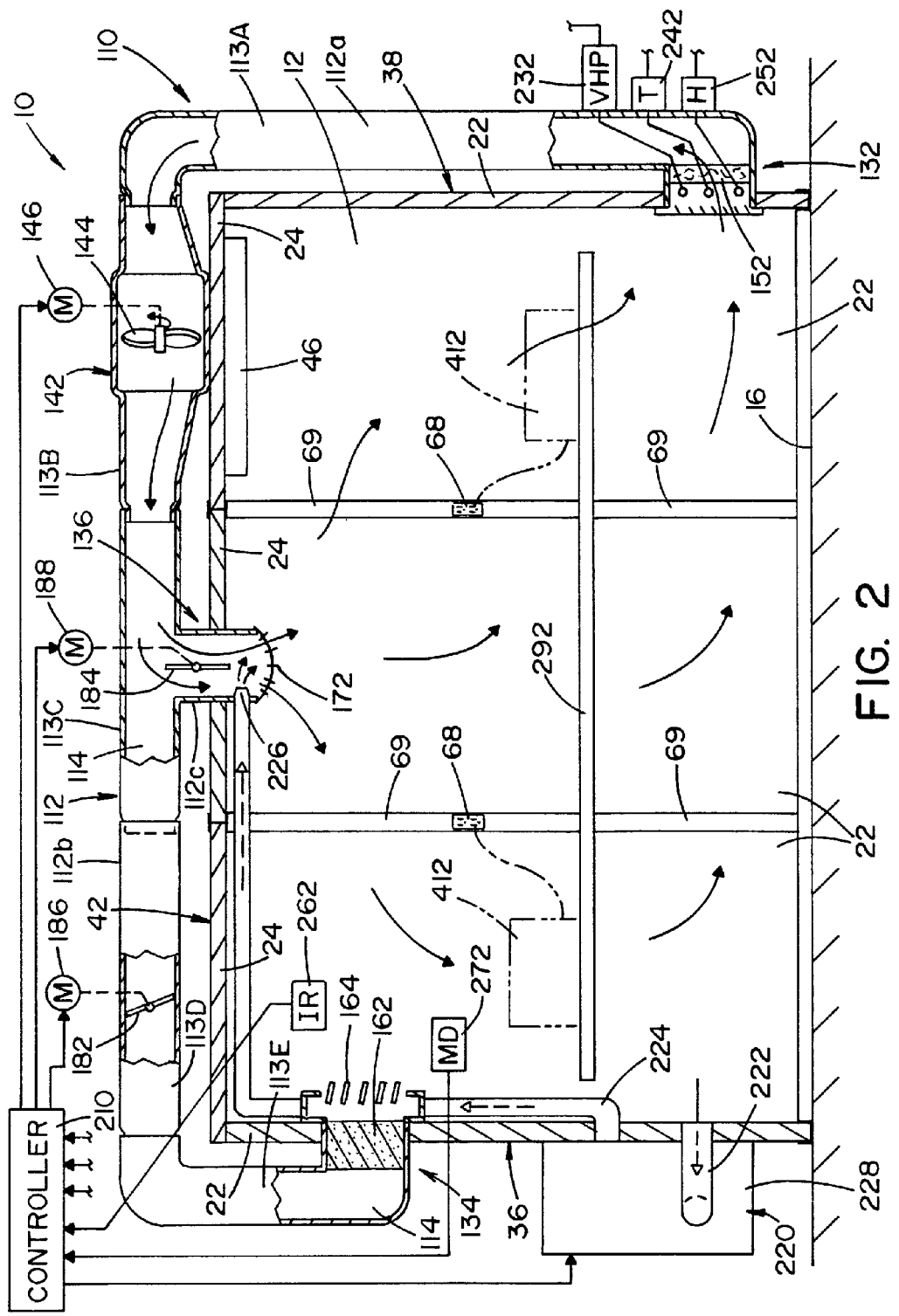
FIG. 2 is a sectional view of the decontamination enclosure shown in FIG. 1, showing the decontamination enclosure during a conditioning phase or a decontamination phase of a decontamination cycle.
Figure 3:
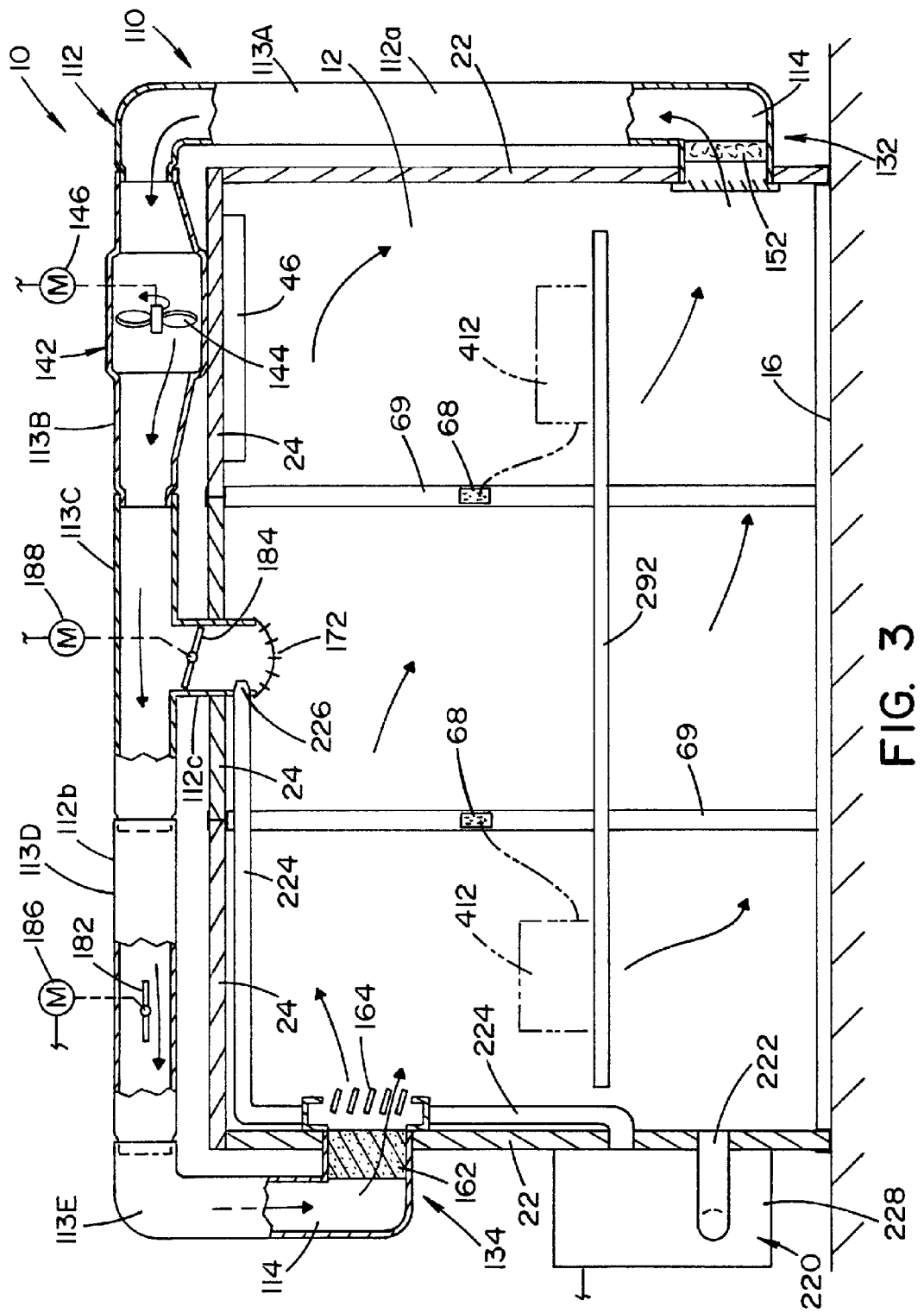
FIG. 3 is a sectional view of the decontamination enclosure shown in FIG. 1 showing the decontamination enclosure during an aeration phase of a decontamination cycle.
Figure 4:
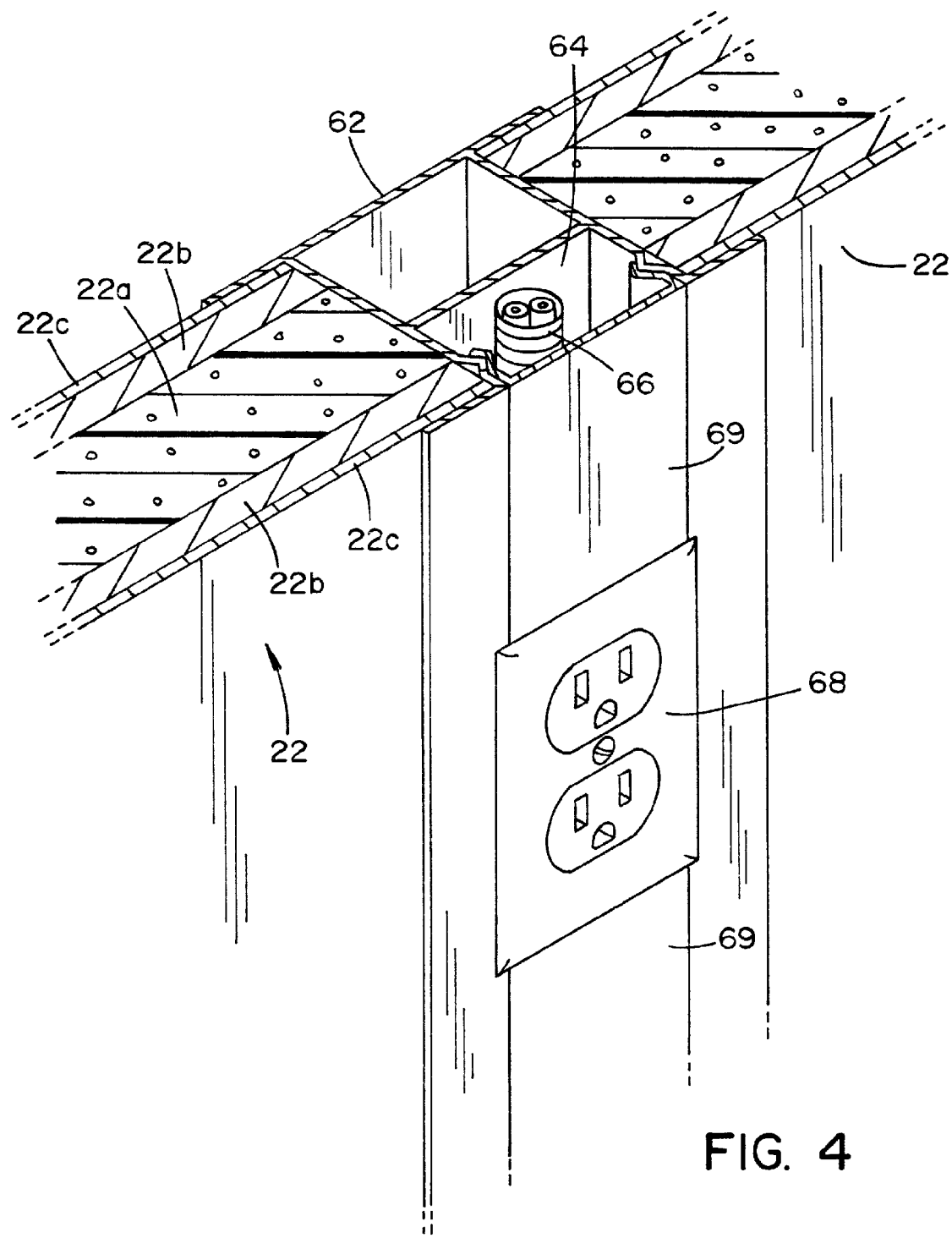
FIG. 4 is a perspective, sectional view of a side wall of the decontamination enclosure showing the construction of the wall panels and a structural member.

Ceiling panels 24 and wall panels 22 are held in place by elongated, structural frame members 62. Each frame member 62, best seen in FIG. 4, defines opposite-facing channels along the sides thereof. Each channel is dimensioned to receive the lateral and longitudinal edges of wall panels 22 and ceiling panels 24, as illustrated in FIG. 4. In the embodiment shown, each frame member 62 is an extruded, metal component having an elongated slot 64 formed along one side thereof. Slot 64 is dimensioned to receive electrical cables 66 and/or electrical outlets 68, as shown in FIG. 4. Elongated cover plates 69 are dimensioned to cover and enclose slots 64 in frame member 62. Electrical cables 66 within enclosure 10 are connected to outlets 68 and light fixtures 46 within chamber 12, as best seen in FIGS. 2 and 3. Electrical cables 66 within enclosure 10 are connected to a power source within room 14 by an external cable 48, which in turn, is connected to an external power source, as illustrated in FIG. 1.

The wall panels and the ceiling panels are rigid structures having an outer surface formed of a material, or coated with a material, that is impervious and inert to vaporized hydrogen peroxide.

In the embodiment shown, each panel 22 is a composite structure comprised of an inner foam core 22a that is sandwiched between two layers of gypsum board 22b. A sheet of aluminum 22c is attached to the outer surface of each layer of gypsum board 22b. The outer exposed surfaces of aluminum sheets 22c are preferably coated with an epoxy layer. Ceiling panels 24 are of similar construction. Each panel 22, 24 has an overall thickness of about three (3) inches. As indicated above, the channels in structural frame members 62 are dimensioned such that the edge of wall panels 22 and ceiling panels 24 fit snuggly therein.

In one embodiment of the present invention, the sides 32, 34, 36, 38 and ceiling 42 of decontamination enclosure 10 are formed of components available from Portafab Modular Building Systems located at 18080 Chesterfield Airport Rd., Chesterfield, Mo. 63005 USA.

A gas circulation system 110 is attached to decontamination enclosure 10 to circulate a carrier gas through chamber 12. In a preferred embodiment, the carrier gas is the air that exists within decontamination enclosure 10. Circulation system 110 includes an elongated duct 112 disposed along the exterior of enclosure 10. In the embodiment shown, duct 112 extends over topside 42 of enclosure 10 from front side 36 of enclosure 10 to back side 38 of enclosure 10. One end of duct 112 is connected to enclosure 10 at a first location 132 (See FIG. 2). In the embodiment shown, first location 132 is disposed on back side 38 of enclosure 10. More specifically, duct 112 is connected to one of wall panels 22 near the lower end thereof, i.e., near floor 16. A first leg 112a of duct 112 extends from first location 132 to a blower assembly 142. Blower assembly 142 includes a fan 144 driven by a motor 146 that is schematically illustrated in FIG. 2. A second leg 112b of duct 112 extends from blower assembly 142 to front side 36 of enclosure 10 where second leg 112b is connected to a wall panel 22 at a second location 134. In the embodiment shown, second location 134 is disposed near the upper end of wall panel 22, i.e., near top side 42 of enclosure 10, as illustrated in the drawings. In the embodiment shown, third leg 112c, i.e., branch leg, is connected to enclosure 10 at a third location 136. Third location 136 is preferably located at a midpoint between front side 36 and back side 38, and between sides 32, 34 of the enclosure 10. In other words, third location 136 is preferably located generally at or near the center of ceiling top side 42 of enclosure 10.

Duct 112 defines an inner passageway 114 (See FIG. 3) that communicates with chamber 12 within enclosure 10 at first location 132, second location 134 and third location 136. Blower assembly 142 is operable to circulate air within chamber 12 in a direction indicated by arrows in the drawing. In this respect, first location 132 is upstream from blower assembly 142 and second location 134 and third location 136 are downstream from blower assembly 142, relative to the direction of airflow.

A filter element 152, best seen in FIGS. 2 and 3, is disposed within duct 112 to filter air drawn from chamber 12 by blower 142. Filter element 152 is preferably disposed in wall panel 22 at the beginning, i.e., the leading, end of first leg 112a of duct 112, so as to filter the air before it is drawn into duct 112. In addition, the location of filter element 152 is preferably located in wall panel 22 to be easily accessible for cleaning or replacement. A catalyst 162 is disposed in duct 112 to break down vaporized hydrogen peroxide used in chamber 12. Catalyst 162 is preferably disposed at the end of second leg 112b of duct 112, i.e., in wall panel 22 at second location 134, as best seen in FIG. 2. In the embodiment shown, a cover 164, consisting of a louvered structure, is provided to direct air flow from duct 112 generally downward.

A diffuser 172 is disposed at third location 136 where third leg 112c of duct 112 communicates with chamber 12. Diffuser 172 is formed as to direct the flow of air or vapor flowing through third leg 112c to generally all areas, i.e., corners, of chamber 12.

Flow control elements 182, 184 are disposed within passageway 114 defined by duct 112. Flow control elements 182, 184 are provided to regulate flow along second leg 112b and third leg 112c of duct 112, respectively. In the embodiment shown, flow control elements 182, 184 are dampers controlled respectively by motors 186, 188, shown schematically in the drawings. Operation of motors 186, 188 is controlled by a controller 210, schematically illustrated in FIG. 2. More specifically, flow control element 182 is disposed in second leg 112b of duct 112 to control airflow therethrough, and flow control element 184 is disposed in third leg 112c of duct 112 to control air flow therethrough. Flow control elements 182, 184 are each movable between a first position and a second position. In the first position, best seen in FIG. 2, flow control element 184 is in an opened position allowing flow through third leg 112c of duct 112 and flow control element 182 is in a closed position preventing flow along second leg 112b of duct 112. When flow control elements 182, 184 are in the first position, and blower assembly 142 is operating, a first flow path, illustrated in FIG. 2, is established from chamber 12 through first leg 112a of duct 112, through third leg 112c of duct 112 and back to chamber 12. When valve elements 182, 184 are in the second position, and blower assembly 142 is operating, a second flow path, illustrated in FIG. 3, is created from chamber 12 through first leg 112a of duct 112 and through third leg 112c of duct 112 and back to chamber 12.

In accordance with one aspect of the present invention, duct 112 is preferably formed in sections. In the embodiment of enclosure 10, shown in FIGS. 1-3, duct 112 is comprised of five (5) duct sections, designated 113A, 113B, 113C, 113D and 113E, best seen in FIG. 2. Horizontal, duct sections 113B, 113C and 113D preferably have a length equal to the width of a wall panel 22 and a ceiling panel 24. Forming duct 112 in sections having dimensions corresponding to the width of wall and ceiling panels 22, 24, allows for easy expansion contraction of enclosure 10, as shall be described in greater detail below.

A vaporized hydrogen peroxide (VHP) generator 220, schematically illustrated in the drawings, is provided on the exterior of enclosure 10. The VHP generator 220 is an apparatus for generating vaporized hydrogen peroxide from liquid hydrogen peroxide. A vaporizer of the type disclosed in U.S. Pat. No. 8,007,717 to Hill finds advantageous application for use on enclosure 10.

An air conduit 222 extends from chamber 12 of enclosure 10 to VHP generator 220 to provide air to generator 220, the air being used as a carrier gas for the vaporized hydrogen peroxide. A VHP feed conduit 224 connects generator 220 to passageway 114 defined by duct 112. In the embodiment shown, VHP feed conduit 224 is disposed within chamber 12. It is contemplated, that VHP feed conduit 224 may also be disposed along the outer surface of enclosure 10. An outlet or nozzle 226 at the end of VHP feed conduit 224 is disposed in passage 114 in third leg 112c of duct 112. Outlet 226 is disposed between flow control element 184 and diffuser 172. In other words, outlet 226 in VHP feed conduit 224 is disposed downstream from flow control element 184 in third leg 112c of duct 112. Generator 220 is preferably enclosed within a cabinet 228 that also contains controller 210. Cabinet 228 also includes storage areas for containers (not shown) of liquid hydrogen peroxide that are used in generator 220.

A VHP sensor 232 is disposed in first leg 112a of duct 112 adjacent to filter element 152. VHP sensor 232 is connected to controller 210 and is operable to provide signals indicative of the amount of vaporized hydrogen peroxide flowing through first leg 112a of duct 112. A VHP sensor (not shown) is also provided around door 52 to detect any leaks that may exist through the door seal. In this respect, the door sensor is connected to controller 210 and is operable to provide signals indicative of the amount of any vaporized hydrogen peroxide flowing past the door seal.

A temperature sensor 242 and a humidity sensor 252 are disposed within leg 112a of duct 112 downstream from filter 152. Temperature sensor 242 and humidity sensor 252 are connected to controller 210 and are operable to provide signals indicative of the temperature and humidity, respectively, within chamber 12. An infrared sensor 262 and a motion detection sensor 272 are also provided within chamber 12. Both sensors 262, 272 are connected to controller 210 and respectively provide signals indicative of the temperature of objects or movement within chamber 12.

Visual indicators 282 are provided on the exterior of enclosure 10 to provide an indication as to the conditions within chamber 12 during a decontamination cycle. More specifically, indicators are lights 282a, 282b, 282c that each illuminate during different stages of the decontamination cycle and indicate when it is safe to enter chamber 12. In the embodiment shown, three (3) colored lights, a red light 282a that signifies an alarm/abort condition, a green light 282b that indicates "power on," and an amber light 282c that signifies vaporized hydrogen peroxide in chamber 12 and door 52 is locked are provided on the exterior of enclosure 10.

A shelf or rack 292 is mounted to wall panels 22 to support medical devices within chamber 12.

A keypad/monitor 296, best seen in FIG. 1, is mounted on the exterior of enclosure 10, to allow a user to input data and commands to controller 210.

Referring now to the assembly and use of decontamination enclosure 10, as indicated above, enclosure 10 is modular and formed of a plurality of like wall and ceiling panels 22, 24 and structural frame members 62. In a preferred embodiment of the present invention, wall panels 22 are generally four (4) feet by eight (8) feet in dimension, and ceiling panels 24 are generally four (4) feet by twelve (12) feet in dimension. At this size, panels 22, 24 can be carried through conventional doorways in existing structures so that enclosure 10 may be assembled and erected within existing rooms of a building structure having a flat, even floor surface. Floor 16 is preferably coated with a material that is not affected by vaporized hydrogen peroxide, such as, by way of example and not limitation, epoxy paint.

In the embodiment shown, enclosure 10 is constructed wherein the front side 36, back side 38 and each first and second side 32, 34 is comprised of three (3) panels that are four (4) feet wide and eight (8) feet high. In this respect, enclosure 10 has an overall dimension of approximately twelve (12) feet by twelve (12) feet by eight (8) feet. Basically, all that is required to install enclosure 10 in an existing room is a flat floor 16 and access to an electrical power source to provide power to light fixture 46 and outlets 68 within enclosure 10. Since wall panels 22 and ceiling panels 24 are of a standard size, duct 112 of circulation system 110 may be pre-formed in sections, as described above, for attachment to a specifically sized enclosure.

As will be appreciated, the length of enclosure 10 may be expanded by merely adding additional wall panels 22 and ceiling panels 24. If duct 112 of circulation system 110 is pre-formed for a standard-sized enclosure, merely adding an appropriately sized duct section to the horizontal lengths of duct 112 that extend over the ceiling of enclosure 10 will adapt a circulation system 110 to the length of longer enclosure 10. The present invention thus provides an enclosure 10 that can be easily modified to different lengths. Moreover, the modular construction of enclosure 10 allows for relatively easy disassembly and movement of enclosure 10 to another location. Still further, the location of enclosure 10 within an existing structure reduces the effects of temperature fluctuations or large changes in humidity as would be experienced if enclosure 10 were located outside of a building and exposed to the environment. Notwithstanding the foregoing, the present invention may be used and assembled outside of a building, so long as the floor is a flat, clean surface. In this respect, decontamination enclosure 10 may be assembled within parking garages, warehouses, or the like.

Referring now to the operation of decontamination enclosure 10, articles to be decontaminated are placed within enclosure 10 through the opening defined by door 52. In this respect, non-critical medical devices, such as beds, stretchers, wheel chairs, IV poles, computers and other devices used in a hospital setting may be placed within chamber 12 of enclosure 10. The size of the article that can be decontaminated is only limited by the size of the door opening. Computers, incubators and electrical devices having fans or blowers and internal air conduits or passageways may be plugged into electrical outlets 68 wherein such devices can operate during decontamination such that internal passageways and conduits can be decontaminated, as shall be described in greater detail below. (FIG. 3 schematically illustrates computer and electrical devices 412 in phantom position on shelf 292).

According to one aspect of the present invention, controller 210 is programmed to perform a decontamination cycle and control operation of generator 220, blower assembly 142 and flow control elements 182, 184. In addition, controller 210 controls electrical outlets 68 within decontamination chamber 12. In accordance with a preferred embodiment of the present invention, the decontamination cycle includes a conditioning phase, a decontaminating phase and an aeration phase.

Once decontamination chamber 12 is loaded with articles to be decontaminated, a decontamination phase is initiated by a hospital worker using a keypad monitor 296 on enclosure 10. Upon initiation of a decontamination cycle, controller 210 activates locking mechanism 56 on door 52 to lock door 52 in a closed position to prevent access into chamber 12. Locking mechanism 56 is of the type often referred to as a "safety lock," that prevents access into chamber 12 from outside of enclosure 10, but allows opening of door 52 from inside chamber 12 at any time. An emergency "stop" button (not shown) is also preferably located within chamber 12. This prevents a worker from accidently being locked into chamber 12 during an initiation of a decontamination cycle, or at any other time.

Prior to initiating a decontamination cycle, controller 210 may be programmed to undertake a room-clear safety check using signals generated from thermal sensor 262 and motion detector sensor 272 to determine if a human, i.e., hospital worker, is present within chamber 12.

According to another aspect of the present invention, controller 210 is programmed to control power to electrical outlets 68 within chamber 12. During this initial chamber-scanning phase, electrical power is terminated to electrical outlets 68 within chamber 12. In this respect, any mechanical device is prevented from operating and any parts, such as fan blades and the like, which would move during operation of the device, would be stationary. Thus, any indication of movement within decontamination chamber 12 at the initiation of a decontamination cycle would be an indication of a person present within decontamination chamber 12. If controller 210 detects a person present within decontamination chamber 12 when a decontamination cycle is initiated, the decontamination cycle is immediately terminated and an indication, such as flashing lights or an alarm (not shown), would be actuated by controller 210. No decontamination cycle would be initiated unless a "room clear" of a worker or user is detected by controller 210.

When a decontamination cycle is initiated and controller 210 determines that no life form is present within decontamination chamber 12, door 52 is locked. Controller 210 insures that flow control elements 182, 184 are in a first position, wherein flow control element 184 allows circulation and flow to diffuser 172 and flow control element 182 prevents flow to catalyst 162. Cover device 164 over catalyst 162 shields and forms a barrier between catalyst 162 and decontamination chamber 12. Blower assembly 142 is activated to circulate the air within chamber 12 along the first flow path, as illustrated in FIG. 2.

A conditioning phase is then initiated by controller 210 which introduces vaporized hydrogen peroxide through VHP feed conduit 224 into the circulating air blown by blower 142 to diffuser 172. During the conditioning phase, generator 220 operates to bring the concentration of vaporized hydrogen peroxide in chamber 12 to a specific, desired decontamination concentration level. The decontamination concentration level is determined by controller 210 based upon the temperature and humidity within chamber 12. In this respect, controller 210 is programmed to maintain the concentration of vaporized hydrogen peroxide within decontamination chamber 12 at a level below that which the vaporized hydrogen peroxide would condense on surfaces within decontamination chamber 12.

Once the desired decontamination concentration layer has been achieved, controller 210 initiates the decontamination phase. During the decontamination phase, controller 210 controls generator 220 to maintain a desired decontamination concentration level within decontamination chamber 12. Vaporized hydrogen peroxide sensors 232 provide signals to controller 210 indicative of the concentration level of a vaporized hydrogen peroxide within decontamination chamber 12. The decontamination phase is maintained for a period of time determined by controller 210 based upon the level of vaporized hydrogen peroxide within chamber 12. As indicated above, during the decontamination phase, cover 164 prevents vaporized hydrogen peroxide within decontamination chamber 12 from being exposed to catalyst 162 at second location 134 within wall panel 22. Optionally, at or before the initiation of the decontamination phase, controller 210 is programmed to electrically energize electrical outlets 68 within decontamination chamber 12. This electrically energizes any electrical equipment plugged into outlets 68. Any fans on the electrical equipment 412 will be activated, thus drawing vaporized hydrogen peroxide through electrical equipment 412 so as to decontaminate the interiors of electrical equipment 412 during the decontamination phase.

After the decontamination phase, an aeration phase is initiated by controller 210. Controller 210 deactivates generator 220 to prevent generation of any additional vaporized hydrogen peroxide, and moves flow control elements 182, 184 to the second position, wherein flow control element 184 obstructs flow to diffuser 172 and flow control element 182 allows flow along the second flow path to catalyst 162. The air in chamber 12 is continuously circulated through catalyst 162 until the vaporized hydrogen peroxide is broken down and reaches a safe level as determined by VHP sensor 232 in first leg 112a of duct 112. Once a safe level is determined to exist by controller 210, blower 142 is deactivated and door locking mechanism 56 is deactivated. Indicator 282c on the exterior of enclosure 10 is caused to turn "off" to indicate that a worker/user can cautiously enter the room per fumigation management plan. If during the decontamination cycle, the door sensor determines a leak of vaporized hydrogen peroxide from enclosure 10, the operation of the decontamination cycle is immediately shut down and the foregoing aeration phase is initiated.

As will be appreciated, at the initiation of the aeration phase, air containing vaporized hydrogen peroxide is blown along second leg 112b of duct 112 to catalyst 162. Because catalyst 162 is disposed at the end of duct 112, i.e., in wall panel 22, the entire length of duct 112 is exposed to vaporized hydrogen peroxide thus insuring that second leg 112b of duct 112 is decontaminated during each decontamination cycle.

The present invention thus provides a decontamination enclosure 10 that can be assembled within rooms or regions of an existing building and that can further be easily expanded or enlarged within such room or region. An enclosure according to the present invention finds advantageous application in existing hospital settings. Decontamination enclosure 10 may also find use in pharmaceutical production and research application where it is highly desirable to employ aseptic "clean side-dirty side techniques" so that articles can be decontaminated prior to moving into a sterile core area of a manufacturing and research facility.

Figure 5:
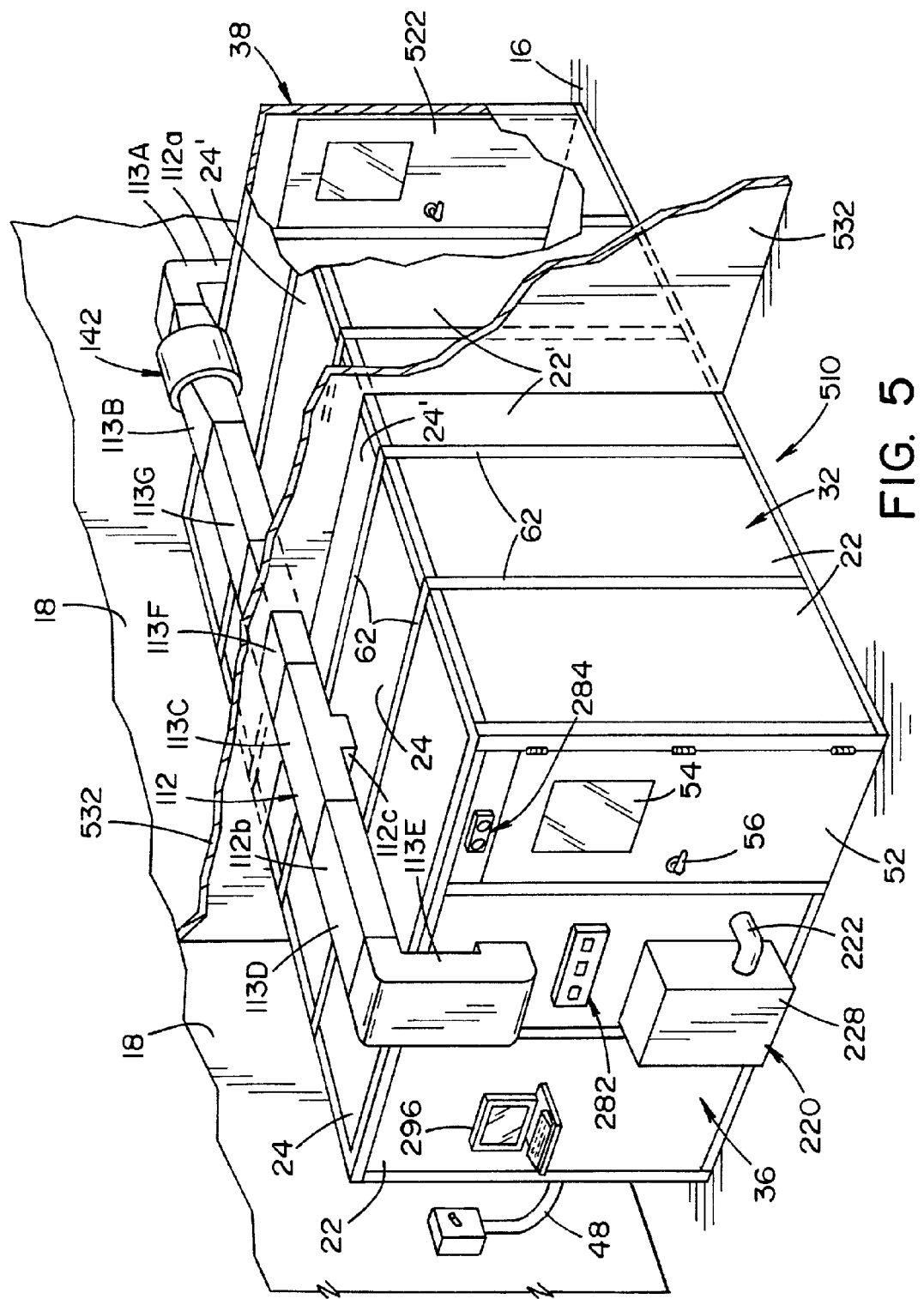
FIG. 5 is a perspective view showing a decontamination enclosure illustrating an alternate embodiment of the present invention.
Figure 6:
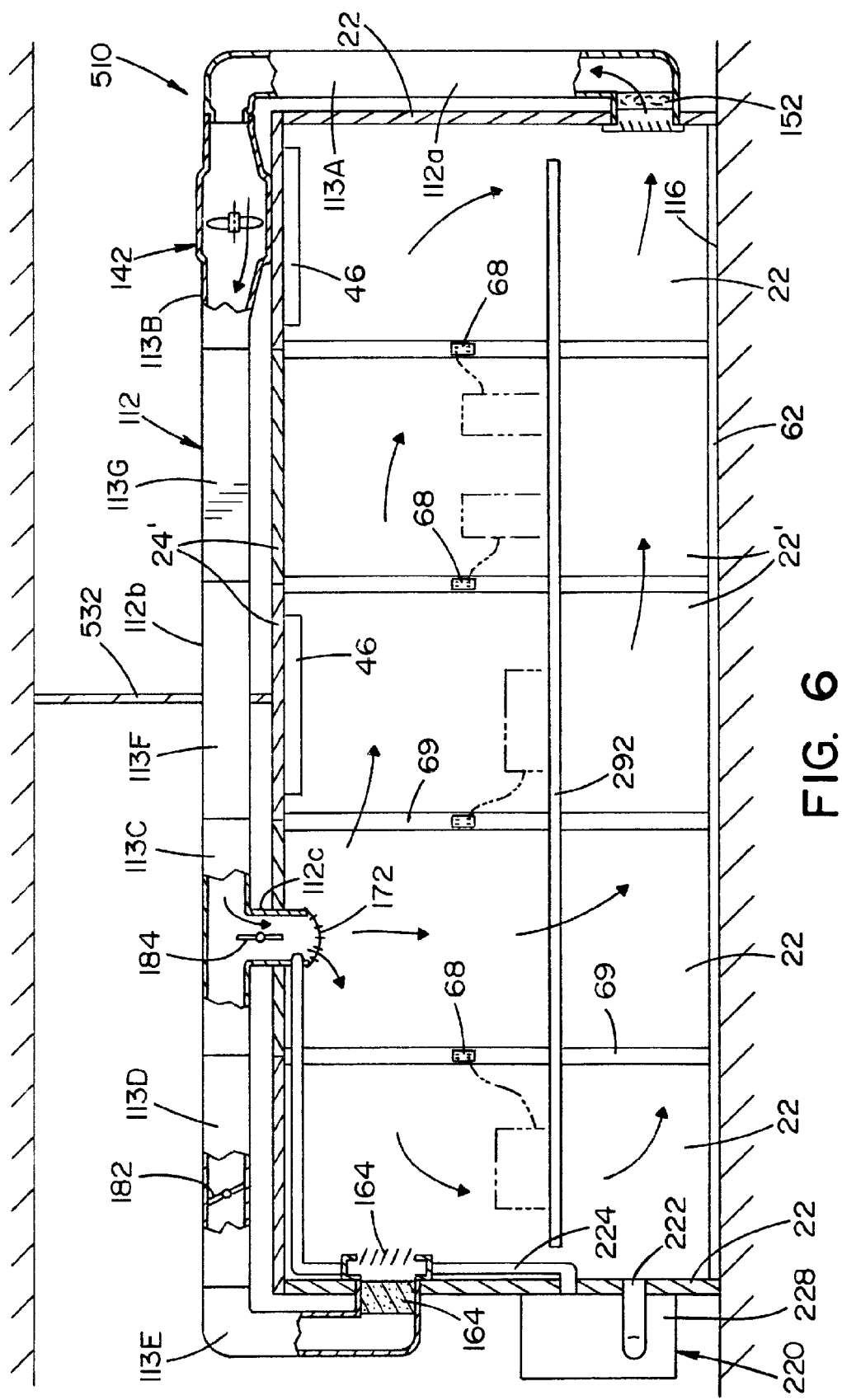
FIG. 6 is a sectional view of the decontamination enclosure shown in FIG. 5.

FIGS. 5 and 6 illustrate a decontamination enclosure 510, illustrating an alternate embodiment of the present invention. Decontamination enclosure 510 is basically a modification of decontamination enclosure 10, wherein additional wall panels 22' and ceiling panels 24' have been added to the original enclosure 10 to form a longer, lengthened enclosure 510. Additional duct sections 113F and 113G have been added to duct 112 to accommodate the longer enclosure 510. In FIGS. 5 and 6, components corresponding to those found in enclosure 10 are designated with like reference numbers. FIGS. 5 and 6 illustrate how an existing or standard-sized enclosure 10 can be easily modified to a larger structure through the addition of modular panels 22', 24' and duct sections 113F and 113G.

In addition to the foregoing, enclosure 510 includes an exit door 522 on back side 38 of enclosure 510. Still further, enclosure 510 is assembled within the room shown with a partition wall 532 erected around enclosure 510 to define a clean area at one end of enclosure 510 from a dirty area at the other end of enclosure 510. Partition wall 532 extends from enclosure 510 to the walls and ceiling of the room. In other words, dirty articles to be decontaminated may be placed into the room using access from a first end of decontamination enclosure 510 and clean articles can be removed from decontamination enclosure 510 in a clean area at the other end of decontamination enclosure 510 by merely isolating each end of decontamination enclosure 510 from the other by partition 532, as shown in FIGS. 5 and 6. In such a configuration, door 52 in the clean area and door 52 in the dirty area are controlled by controller 210 such that the doors 52 cannot be opened at the same time. Door 52 in the clean area will not open until a successful decontamination cycle has been completed. When door 52 in the clean area is opened, door 52 in the dirty area cannot open and vice versa.

It is also contemplated that decontamination enclosures 10 or 510 can be fitted with an RFID tag reader or bar code reader to track the frequency of the decontamination of articles decontaminated therein. In this respect, each item within a hospital facility may be fitted with an RFID tag or bar code for monitoring and data can be maintained as to when each article was decontaminated and when an article may be due for another decontamination cycle.

In addition to decontaminating medical devices and equipment, decontamination enclosures 10 or 510 can also be used to decontaminate items and equipment before they are disposed of so as to prevent pathogenic contamination into trash receptor bins. Still further, decontamination enclosures 10 or 510 can be used to treat the external surfaces of various canned or imperviously packaged drug and nutritional items that are unopened, but have been removed from a contaminated patient area. Even further, decontamination enclosures 10 or 510 can be used by manufacturers of various equipment (medical, pharmaceutical) to eliminate any surface contamination on the equipment prior to servicing of the equipment.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, enclosure 10 may be formed from wall panels 22 and ceiling panels 24 attached to one or more walls of an existing room, wherein the existing walls form part of enclosure 10. It is intended that all such modifications and alterations be included insofar as they come within the scope of the invention as claimed or the equivalents thereof.

Having described the invention, the following is claimed:

1. A decontamination enclosure, comprised of:
a plurality of preformed, rigid structural panels joined together to form a modular structure defining a totally enclosed chamber, a door formed in at least one of said panels, said door movable between an opened position and a closed position to allow access to said chamber;
a circulation system attached to said structure for circulation of gas through said chamber, said circulation system having:
a duct disposed along the exterior of said structure, said duct being connected to said enclosure and communicating with said chamber at a first location to define an outlet from said chamber and being connected to said enclosure and communicating with said chamber at a second location and at a third location to define inlets to said chamber; and
a blower disposed in said duct for conveying a stream of gas through said duct in a first direction, said blower disposed in said duct downstream from said first location and upstream from said second and third locations;

a catalyst disposed in said duct at said second location;

a vaporized hydrogen peroxide generator connected to said duct for introducing vaporized hydrogen peroxide into said stream of gas at said third location; and a controller for controlling the amount of vaporized hydrogen peroxide introduced into said chamber and for controlling the flow of said gas to said second location and said third location, wherein said structure formed by said plurality of preformed, rigid structural panels supports said circulation system, said catalyst, said vaporized hydrogen peroxide generator and said controller.

2. A decontamination enclosure as defined in claim 1, wherein said circulation system includes flow control elements within said duct for selectively controlling flow to said second location and said third location.

3. A decontamination enclosure as defined in claim 2, wherein said flow control elements are controlled by said controller and define a first gas flow path when said control elements are in a first position and second gas flow path when said control elements are in a second position.

4. A decontamination enclosure as defined in claim 2, wherein said flow control elements are dampers disposed in said duct.

5. A decontamination enclosure as defined in claim 3, wherein said first gas flow path is a path from said chamber through said duct and back into said chamber at said second location.

6. A decontamination enclosure as defined in claim 3, wherein said second gas flow path is a path from said chamber through said duct and back into said chamber at said third location.

7. A decontamination enclosure as defined in claim 1, further comprising a filter in said duct at said first location to filter said gas flow from said chamber into said duct.

8. A decontamination enclosure as defined in claim 1, further comprising a temperature sensor and a humidity sensor in said chamber, said sensors connected to said controller.

9. A decontamination enclosure as defined in claim 1, further comprising a hydrogen peroxide sensor disposed within said duct at said first location.

10. A decontamination enclosure as defined in claim 1, further comprising a door locking mechanism for locking said door in a locked condition during a decontamination cycle.

11. A decontamination enclosure as defined in claim 1, wherein said structure includes lighting fixtures within said chamber.

12. A decontamination enclosure as defined in claim 1, wherein said structure includes electrical outlets within said chamber.

13. A decontamination enclosure as defined in claim 1, wherein the dimensions of said chamber can be increased by adding additional panels to said structure.

14. A decontamination enclosure as defined in claim 1, wherein said enclosure is dimensioned to be assembled within an existing room or region of a building.

15. A decontamination enclosure as defined in claim 1, wherein said enclosure further includes:

a plurality of elongated, structural frame members, each of said frame members defining opposite-facing channels along the sides thereof for receiving lateral and longitudinal edges of said preformed panels.

16. A decontamination enclosure as defined in claim 15, wherein at least one of said frame members includes a slot formed along one side thereof for receiving an electrical cable.

* * * * *